(12) United States Patent
Chou et al.

(10) Patent No.: US 12,105,333 B2
(45) Date of Patent: Oct. 1, 2024

(54) OPTICAL ASSEMBLIES COMPRISING A PRISM

(71) Applicant: ROCKLEY PHOTONICS LIMITED, Altrincham (GB)

(72) Inventors: Chia-Te Chou, Brea, CA (US); William Vis, Pasadena, CA (US); Alexander Gondarenko, San Jose, CA (US); Shuhe Li, Pasadena, CA (US); David McCann, Pasadena, CA (US); Haydn Frederick Jones, London (GB); Alexander Fast, Aliso Viejo, CA (US)

(73) Assignee: Rockley Photonics Limited, Altrincham (GB)

(*) Notice: Subject to any disclaimer, the term of this patent is extended or adjusted under 35 U.S.C. 154(b) by 0 days.

(21) Appl. No.: 18/271,217

(22) PCT Filed: Jan. 6, 2022

(86) PCT No.: PCT/IB2022/000029
§ 371 (c)(1),
(2) Date: Jul. 6, 2023

(87) PCT Pub. No.: WO2022/149051
PCT Pub. Date: Jul. 14, 2022

(65) Prior Publication Data
US 2024/0077688 A1 Mar. 7, 2024

Related U.S. Application Data

(60) Provisional application No. 63/134,899, filed on Jan. 7, 2021.

(51) Int. Cl.
*G02B 6/42* (2006.01)

(52) U.S. Cl.
CPC .......... *G02B 6/4214* (2013.01); *G02B 6/428* (2013.01)

(58) Field of Classification Search
CPC ....................................................... G02B 6/42
(Continued)

(56) References Cited

U.S. PATENT DOCUMENTS 5,347,606 A * 9/1994 Johansen ............. G02B 6/3801
385/95
6,021,238 A 2/2000 Spaeth
(Continued)

FOREIGN PATENT DOCUMENTS

CN 209819269 U * 12/2019
JP 2007127878 A * 5/2007
WO WO-2017025515 A1 * 2/2017 ........... G02B 6/4214

OTHER PUBLICATIONS

International Search Report and Written Opinion of the International Searching Authority, mailed Jun. 9, 2022, corresponding to PCT/IB2022/000029, 11 pages.

*Primary Examiner* — Kaveh C Kianni
(74) *Attorney, Agent, or Firm* — Lewis Roca Rothgerber Christie LLP

(57) ABSTRACT

An optical assembly (100) for use in a wearable device is provided, the assembly (100) comprising: a prism (104), a photonic integrated chip, PIC (108), a substrate layer (106), and a lid (102); wherein the PIC (108) is mounted onto the substrate layer (106); the prism (104) comprising: (i) a first input/output surface (112) optically coupled to the PIC (108), and (ii) a second input/output surface (114) optically coupled to the lid (102), the second input/output surface (114) orientated perpendicularly to the first input/output surface (112), and wherein the prism (104) provides an optical path and reflects a percentage of light from the first (Continued)

input/output surface (112) to the second input/output surface (114). Methods of manufacturing such an optical assembly are also provided.

17 Claims, 11 Drawing Sheets

(58) Field of Classification Search
USPC .......................................................... 385/36
See application file for complete search history.

(56) References Cited

U.S. PATENT DOCUMENTS

| | | | | |
|---|---|---|---|---|
| 6,789,959 | B1* | 9/2004 | Conn | G02B 6/4214 |
| | | | | 385/94 |
| 7,466,880 | B2* | 12/2008 | Windover | H04B 10/801 |
| | | | | 385/129 |
| 8,861,917 | B2* | 10/2014 | Kim | G02B 6/1226 |
| | | | | 385/131 |
| 11,175,447 | B1* | 11/2021 | Pynn | H01L 33/32 |
| 11,320,588 | B1* | 5/2022 | Mazed | G16H 10/40 |
| 11,362,237 | B2* | 6/2022 | Hahn | H01L 33/46 |
| 11,885,887 | B1* | 1/2024 | Mazed | G01S 17/34 |
| 11,892,746 | B1* | 2/2024 | Mazed | G02F 1/225 |
| 2009/0010589 | A1* | 1/2009 | Robertson | G01N 21/553 |
| | | | | 385/12 |
| 2014/0131549 | A1* | 5/2014 | Kaskoun | H01L 25/50 |
| | | | | 250/206 |
| 2015/0133609 | A1* | 5/2015 | Jiang | C08G 73/0266 |
| | | | | 528/331 |
| 2016/0291268 | A1* | 10/2016 | Shimura | G02B 6/4246 |
| 2018/0239096 | A1* | 8/2018 | Houbertz | G02B 6/4214 |
| 2018/0246279 | A1* | 8/2018 | Florian Lohse | G02B 6/1228 |
| 2018/0246286 | A1* | 8/2018 | Lohse | G02B 6/305 |
| 2019/0052362 | A1* | 2/2019 | Peterson | G02B 27/0961 |
| 2019/0115995 | A1* | 4/2019 | Sahni | G02B 6/272 |
| 2020/0069225 | A1* | 3/2020 | Vizbaras | G01J 3/42 |
| 2020/0119828 | A1* | 4/2020 | Sahni | G02B 6/4246 |
| 2020/0183085 | A1* | 6/2020 | Mentovich | G02B 6/1223 |
| 2020/0241222 | A1* | 7/2020 | Wang | G02B 6/4226 |
| 2022/0003925 | A1* | 1/2022 | Wang | G02B 6/122 |
| 2022/0104342 | A1* | 3/2022 | Verslegers | G02B 6/4245 |
| 2022/0128782 | A1* | 4/2022 | Goldis | G02B 6/4244 |
| 2022/0196931 | A1* | 6/2022 | Li | G02B 6/4206 |

* cited by examiner

OPTICAL ASSEMBLIES COMPRISING A PRISM

CROSS-REFERENCE TO RELATED APPLICATIONS

The present application is a U.S. National Phase Patent Application of International Application No. PCT/IB2022/000029, filed on Jan. 6, 2022, which claims priority to and the benefit of U.S. Provisional Application No. 63/134,899, filed Jan. 7, 2021, the entire content of each of which is incorporated herein by reference.

FIELD OF THE INVENTION

The present invention relates to optical assemblies for use in a wearable device, where the optical assembly includes a prism and a photonic integrated chip (PIC). The present invention also relates to the methods of fabricating these optical assemblies for use in such devices.

BACKGROUND OF THE INVENTION

Semiconductor light emitters can be grouped into two main classes: namely edge-emitters and surface-emitters. Edge-emitters, such as edge-emitting lasers (also known as in-plane lasers) work by emitting light in a direction along a wafer surface of a semiconductor chip (e.g. from which the laser light is generated). The light is usually reflected or coupled out at a cleaved edge of the semiconductor structure (e.g. a semiconductor chip). Within the edge-emitter's semiconductor structure, the light is typically guided in a waveguide. Conversely, surface-emitters work by allowing generated light to propagate in a direction perpendicular to that of the semiconductor wafer surface.

Edge-emitting lasers are one of the original, and still one of the most widely used, forms of semiconductor lasers. However, in recent times it has been found that they are not conducive to compact integration in certain optoelectronic devices, for example in compact integration inside certain wearable optical devices, such as wearable fitness trackers and smart watches, etc. One reason for this is that the compact integration of these devices often requires an out-of-plane turning of emitted and/or generated light across a broad wavelength, which is difficult to achieve using conventional edge-emitting semiconductor structures. Herein, "out-of-plane turning" may be understood to refer to redirection of the resulting laser beam into a direction out of the plane of the semiconductor chip in which the laser light is generated.

Other reasons are that, in some cases, a compact integration within these types of devices requires a compact semiconductor assembly to comprise a PIC that is wire-bonded directly onto a printed circuit board (PCB), such that the emitted light has an optical path that must be turned "up" (e.g. the optical path is turned upwards, i.e. away from the PCB within the assembly) for that device to function properly. In this type of compact semiconductor assembly, turned down light would have an optical path that is subsequently blocked by the PCB and would therefore be unsuitable for use in such a device. Alternatively, out-of-plane optical turning of generated light may instead involve turning the light "down" (e.g. the optical path is turned downwards, i.e. away from the PCB within the assembly).

In regard to protecting the optical path of the emitted/generated light, the turning of light (i.e. either turning it up or turning it down) can happen in air, or it can happen in a higher refractive index material. Using a higher refractive index material is often preferred in order to reduce beam divergence. However, problems are known to arise in known semiconductor fabrication processes, particularly with respect to the fabrication step of filling the intended optical path with an optical epoxy, as this fabrication method requires a relatively large amount of this material to be used, which can be very challenging to control within certain tolerances. Moreover, the assembly of optical parts in a compact semiconductor assembly requires a precise alignment in order to minimize signal loss. Typically, known flip-chip assemblies have a coarse alignment for dies, but at a larger scale than micromirrors. Passive alignment structures enable fine alignment but require a high dimensional accuracy.

Furthermore, requirements of wearable optical devices (and thus, requirements of the compact semiconductor assembly used in these device) include: being durable (e.g. particularly if the wearable device is a fitness tracker), being resistant to any ingress of foreign bodies (e.g. being waterproof/water resistant), and being capable of delivering/emitting light at a minimal loss and at a high accuracy.

It is with these problems in mind, and a knowledge of the shortcomings of known prior art semiconductor assemblies and their fabrication methods, that the inventors have devised the present invention.

SUMMARY OF THE INVENTION

Broadly speaking, the present invention aims to address the problems outlined in the previous section by providing an optical assembly in which a prism is coupled to a photonic integrated chip, and acts to redirect the path of the laser light out of the plane of the photonic integrated chip.

Specifically, the present invention aims to solve the above problems by providing, according to a first aspect, an optical assembly for use in a wearable device, the assembly comprising: a prism, a photonic integrated chip, PIC, a substrate layer, and a lid; wherein the PIC is mounted onto the substrate layer; the prism comprising: i) a first input/output surface optically coupled to the PIC, and ii) a second input/output surface optically coupled to the lid, the second input/output surface orientated perpendicularly to the first input/output surface, and wherein the prism provides an optical path and reflects a percentage of light from the first input/output surface to the second input/output surface.

Thus, the prism may have a total of two input/output surfaces: the first input/output surface and the second input/output surface, which are located adjacent to each other and are orientated perpendicularly, or near perpendicularly, to each other, such as at 80° to 100° to each other, for example.

Such an optical assembly enables an out-of-plane optical turning of generated light, such as a generated laser output. The present invention overcomes the shortcomings of known edge-emitting semiconductor structures by enabling a compact integration within wearable optoelectronic devices. Specifically, the prism of the claimed assembly provides an optical path that enables the generated light to be turned up within the assembly during its operation. As a result, the claimed optical assembly enables the PIC to be wire-bonded directly onto the PCB. In this way, the claimed optical assembly benefits from being compactly integrated within the wearable device itself. Alternatively, out-of-plane optical turning of generated light may instead involve turning the light "down" (e.g. the optical path is turned downwards, i.e. away from the PCB within the assembly). In this embodiment, the light could then be directed towards the skin of a wearer of the wearable optoelectronic device (e.g. at the wearer's wrist) through a hole formed in the PCB. The light could then be directed to the skin when the PCB is inverted.

Optional features of the invention will now be set out. These are applicable singly or in any combination with any aspect of the invention.

In some embodiments, a first layer of refractive index-matched optical material may be formed between the first input/output surface of the prism and the PIC, and a second layer of refractive-index matched optical material may be formed between the second input/output surface of the prism and the lid.

In some other embodiments, the first layer of refractive index-matched optical material could be air with a small angle between the prism and the lid's surface to minimize interfering back reflection.

By using refractive index-matched optical material at the first and at the second input/out surfaces of the prism, the claimed assembly reduces signal loss (e.g. due to diffraction, back or internal reflections, etc.) and subsequently maximizes the efficiency and delivery of the laser power of the emitted laser light.

In these embodiments, the first layer of layer of refractive-index matched optical material may comprise a layer of epoxy and the second layer of refractive-index matched optical material may comprise a layer of silicone gel.

In alternative embodiments, the first layer of layer of refractive-index matched optical material may instead comprise a layer of silicone gel and the second layer of refractive-index matched optical material may instead comprise a layer of epoxy.

Silicone gel and epoxy are both durable and robust materials. By using silicone gel and/or epoxy layers within the compactly integrated semiconductor structure, the optical assembly improves the reliability of the performance of the optical assembly and, with it, also improves the performance of the wearable device itself. Furthermore, use of these materials reduces the overall cost of manufacture, making the fabrication process both easier and at a lower cost, without requiring additional development or modification of the existing semiconductor fabrication methods.

In some embodiments, the prism further may comprise: iii) a third input/output surface optically coupled to a back region and orientated 45° to both the i) first input/output surface and ii) the second input/output surface, and wherein a second percentage of light may be transmitted through the third input/output surface into the back region.

In other embodiments, the third input/output surface is optically coupled to a back region and orientated at an angle to both the i) first input/output surface and ii) the second input/output surface, where the angle is not 45°. This angle may be any other degree (°) value, such as any other degree value in the range between 0° to 90° inclusive, for example any other angle value in the range between 5° and 85° inclusive. The angle may be any other value in the range between 10° and 80° inclusive, such as any other value in the range between 15° to 75° inclusive. The angle may be any other value, such as any other value in the range between 20° to 70° inclusive, for example any other angle value in the range between 25° and 65° inclusive. The angle may be any other value in the range between 30° and 60° inclusive, such as any other value in the range between 35° to 55° inclusive, for example any other angle value between 40° to 50° inclusive.

In these embodiments, the prism has a total of three input/output surfaces. There is the first input/output surface and the second input/output surface, which are located adjacent to each other and orientated perpendicularly, or at least near perpendicularly, to each other. In addition, there is a third input/output surface which may be located opposite to, and orientated at a 45° angle (or an angle of approximately 45°, in the event that the first input/output surface and the second input/output surface are not exactly perpendicular to each other) to, both the first input/output surface and the second input/output surface. In these embodiments, the prism provides an optical path for light received at the first input/output surface and reflects a first percentage of light at the third input/output surface towards the second input/output surface. In addition, the second percentage of light is transmitted through the third input/output surface into the back region. Herein, it should be understood that the light is internally reflected from the inside of the third input/output surface.

In this way, the prism acts as an optical tap in that it splits the incident light into two paths at the third input/output surface. In other words, the prism splits the incident light into a first percentage of light (which is then reflected towards the second input/output surface) and taps off the second percentage of light (which is then transmitted through the third input/output surface into the back region).

The rays of laser light emerging from the PIC will not be parallel, but rather will be distributed across a range of angles from a beam axis, effectively in a cone of light. In the cone of light (or light cone), some of the rays will be incident on the inside of the third input/output surface at an angle of incidence which is greater than the critical angle associated with the boundary between the prism (i.e. a higher refractive index material) and the air outside the prism (i.e. a lower refractive index material). Herein, the angle of incidence is the angle measured relative to the normal to the third input/output surface. These rays will undergo total internal reflection, and will be reflected from the inside of the third input/output surface at an angle equal to their respective angles of incidence.

Some of the light rays in the light cone will be incident on the inside of the third input/output surface at an angle which is less than the critical angle. The majority of this light will be transmitted (undergoing refraction) by the third input/output surface, and will pass out of the prism. However, a small proportion of this light will be specularly reflected from the inside of the third input/output surface of the prism at an angle equal to the incidence of the respective ray.

The first percentage of light is made up of the light which is totally internally reflected and the light which is specularly reflected by the third input/output surface of the prism. The second percentage of light is made up of the light which is transmitted (i.e. refracted) through the third input/output surface towards the back region.

It should be noted that rays which are incident at exactly the critical angle are refracted along the third input/output surface. The critical angle may be calculated as:

$$\theta_{Critical} = \arcsin\left(\frac{n_2}{n_1}\right)$$

Here, $\theta_{Critical}$ is the critical angle, $n_1$ is the refractive index of the material of the prism, and $n_2$ is the refractive index of the surrounding medium, in this case air, for which $n_2 \approx 1$.

In some embodiments, the optical path could also be enabled by creating an angle between the prism and the lid. In these embodiments, the prism may have a total of three input/output surfaces. For example, there may be a first input/output surface, a second input/output surface which is located adjacent to the first input/output surface, and a third input/output surface which is located opposite to, and orientated at a 45° angle (or an angle of approximately 45°, in the event that the first input/output surface and the second input/output surface are not exactly perpendicular to each other) to, both the first input/output surface and the second input/output surface.

In these embodiments, the second input/output surface of the prism may be orientated at angle θ to the lid. In some embodiments, the angle θ may be any degree (°) value in the range between 1° and 45° inclusive, such as any value in the range between 5° to 40° inclusive, for example any value in the range between 10° and 35° inclusive. The angle θ may be any value in the range between 15° and 30° inclusive, such as any value in the range between 20° to 25° inclusive. In other embodiments, the angle θ may be, for example, any one of the following degree (°) values: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45.

In one embodiment the angle θ is 8°. In other embodiments the angle θ is approximately 8°, such as being any value in the range between 6° to 10°, for example.

Advantageously, by orientating the prism at angle as previously discussed, the optical assembly can minimize interfering back reflection and eliminate the need for a polymer fill, for example. Orientating the prism at angle in this way also eliminates the need for use of an index matching epoxy between the prism and the lid as an air wedge is formed therebetween, i.e. within the cavity subtended by angle θ (i.e. is formed within the angle between the second input/output surface of the prism and the lid). This advantageously removes the effect of the back reflection of the light. The thermal mechanical stress from outside of the package does not propagate to the prism and the PIC.

In some embodiments, the back region comprises a light barrier wall and a first photodiode mounted to the substrate layer, and the second percentage of transmitted light may be scattered from the light barrier wall.

In other embodiments, the barrier wall is intended to stop stray light from reaching one or more of the sensor photodiode(s) so that of the most light reaches these photodiodes by reflection from another surface, (e.g. from the wearer's skin). In this embodiment, the barrier wall is not meant to stop light from being partially reflected to a 'monitor photodiode' (hereafter referred to using the acronym MPD). The terms "monitor photodiode", "MPD", and "sensor photodiode(s)" are interchangeable and all refer to the same thing.

The light barrier may be an internal wall or region within the semiconductor structure that light cannot pass through. The light barrier may be configured to scatter and/or reflect some or all incident light on it. In some embodiments, the light barrier wall may absorb the light that hits it and/or is incident on it.

In some embodiments, the back region further comprises a second photodiode mounted to the light barrier wall and may be configured to receive the second percentage of light which is transmitted through the third input/output surface. In other embodiments, the second photodiode could also be mounted to the PCB.

In other embodiments, the first photodiode and second photodiode may be any light (or photon) detecting module that may be integrated into a semiconductor circuit, such as a semiconductor diode, a photodetector, or any semiconductor p-n junction device that converts light into an electrical current.

In other embodiments, the prism may be formed of a material comprising a refractive index, $n_1$, with any value in the range of 1.5 to 1.8 inclusive. For example, the $n_1$ may be any value in the range of 1.55 to 1.75 inclusive, for example any value in the range of 1.6 to 1.7 inclusive, such as 1.65. The value of $n_1$ may be, for example, any one of the following values: 1.50, 1.51, 1.52, 1.53, 1.54, 1.55, 1.56, 1.57, 1.58, 1.59, 1.60, 1.61, 1.62, 1.63, 1.64, 1,65, 1.66, 1.67, 1.68, 1.69, 1.70, 1.71, 1.72, 1.73, 1.74, 1.75, 1.76, 1.77, 1.78, 1.79, 1.80.

In some embodiments the lid may be formed of glass.

In some embodiments, the lid may be made from any from any optically transparent material, such as an optically clear polymer or crystal.

In other embodiments the prism may be formed of glass.

In other words, the claimed invention provides a broadband reflective micro-mirror, where full protection of optical light is enabled by flipping a glass prism so the light travels through the glass. The production of glass prisms with an optical quality facet is an established technology that can be fabricated at scale and therefore easily incorporated into the fabrication method at a minimal cost.

In other embodiments, the prism may be formed of any other optically transparent materials that is also configured to refract white light into its constituent colours. In addition to glass, other possible prism materials include acrylic or fluorite, for example. It will be appreciated that this is not an exhaustive list of possible materials.

In some embodiments the substrate layer may either be (or comprise) a printed circuit board (PCB) of the wearable device or a sub-mount layer bonded to a PCB of the wearable device.

In other embodiments the substrate layer may comprise: a BOX layer and a silicon layer mounted onto the BOX layer.

In some embodiments the prism may have total length (L) that may be any value in the range between 2.5 mm and 1.80 mm, and may have a total height (H) that may be any value in the range between 1.00 mm, and 1.05 mm. For example, the prism may have total length (L) of 2.00 mm and may have a total height (or width) of 1.00 mm. In other examples, the prism has a total length (L) of 1 mm and a total height (H) of 0.5 mm.

In other embodiments the length of the first input/output surface formed between the PIC and the prism may be any value in the range between 0.32 mm, and 0.37 mm. The length of the first input/output surface corresponds to the length of the contact region where a surface of the PIC is in contact with a surface of the prism.

According to a second aspect of the invention, there is a method of fabricating the optical assembly of the first aspect of the invention, where the method comprises the following steps: (i) forming the substrate layer, (ii) forming an intermediate layer, (iii) bonding the intermediate layer to the substrate layer, (iv) bonding the PIC (108) to the intermediate layer, (v) bonding the prism to the PIC using a layer of epoxy at the first input/output surface, and (vi) bonding the lid to the prism using a layer of silicone gel at the second input/output surface.

In other embodiments, the above-mentioned method steps (i) to (vi) of fabricating the optical assembly are reversed.

In some embodiments, the method comprises the following steps (i) forming the substrate laye, (ii) forming an intermediate layer, (iii) bonding the prism to the PIC using a layer of epoxy at the first input/output surface, (iv) bonding the lid to the prism using a layer of silicone gel at the second input/output surface, (v) bonding the PIC to the intermediate layer, and (vi) bonding the intermediate layer to the substrate layer.

The prism may be directly attached to the PIC using a refractive index matching epoxy. Alignment of the prism to the PIC may be achieved by using a prism supporting submount (or subcarrier). In other embodiments, if the prism is be small enough (and therefore light enough) the subcarrier may not be needed to support its weight as the adhesive quality of the epoxy bond is strong enough to hold prism's weight. The other end of the prism is refractive index matched to the glass lid by a layer of the silicone gel.

In the present context, the terms "submount" or "subcarrier" are used to refer to a component on which the third input/output surface of the prism may rest in order to support it against gravity, thereby ensuring that neither the first input/output surface becomes separated from the PIC, nor the second input/output surface becomes separated from the lid. Accordingly, the subcarrier may comprise a base surface arranged to contact or rest on an upper surface of the substrate, and an oblique surface on which the third input/output surface of the prism is configured to rest, the oblique surface forming the same angle with the base surface as the second input/output surface forms with the third input/output surface.

The order of manufacture may be that the prism is first epoxy bonded onto the PIC first, using a subcarrier for alignment if necessary. Thereafter, silicone gel may be added onto the prism before attaching the glass lid.

According to a third aspect of the invention, there is alternative method of fabricating the optical assembly of the first aspect of the invention, where the method comprises the following steps: (i) forming a substrate layer, (ii) bonding the PIC to the substrate layer, iii) bonding the prism to the PIC using a layer of silicone gel at the first input/output surface, and iv) bonding the lid to the prism using a layer of epoxy at the second input/output surface.

In other embodiments, the above-mentioned method steps (i) to (iv) of fabricating the optical assembly are reversed.

In some embodiments, the method comprises the following steps: (i) forming a substrate layer, (ii) bonding the prism to the PIC using a layer of silicone gel at the first input/output surface, bonding the PIC to the substrate layer, (iii) bonding the lid to the prism using a layer of epoxy at the second input/output surface bonding the prism to the PIC using a layer of silicone gel at the first input/output surface, and (iv) bonding the PIC to the substrate layer bonding the lid to the prism using a layer of epoxy at the second input/output surface.

In this embodiment, the prism is instead attached to the glass lid by the refractive index matched epoxy. Refractive indexed matched silicone gel is instead used between the PIC and the other end of the prism (i.e. at the first input/output surface). Alternatively, in other embodiments, the first input/output surface can be left as an air gap (with no silicone gel present) which allows for stray light to be measured by an MPD.

In other words, in this alternative method of fabrication, there is an epoxy bond of the prism onto the lid while attaching PIC to PCB and wire-bond. The silicone gel is added before the glass lid attached.

According to a fourth aspect of the invention, there is an optical assembly comprising: a prism, a photonic integrated chip, PIC, and a substrate layer; wherein the PIC is mounted onto the substrate layer; the prism comprising: (i) a first input/output surface optically coupled to the PIC, (ii) a second input/output surface, the second input/output surface orientated perpendicularly to the first input/output surface, and (iii) a third input/output surface optically coupled to a back region and orientated 45° to both the first input/output surface and the second input/output surface, wherein: the prism provides an optical path for light received at the first input/output surface and reflects a first percentage of light at the third input/output surface towards the second input/output surface; and a second percentage of light is transmitted through the third input/output surface into the back region.

In this way, the fourth aspect of the invention is identical to the first aspect of the invention, but with addition of the, previously discussed, "optical tap" feature that is configured to splits the incident light into two paths at the third input/output surface; i.e. the prism splits the incident light into a first percentage of light (which is then reflected towards the second input/output surface) and "taps off" the second percentage of light (which is then transmitted through the third input/output surface into the back region). More detail about the splitting of light into the first reflected percentage and the second transmitted (i.e. refracted) percentage is provided earlier in the application.

In some embodiments the optical assembly further comprises a lid optically coupled to the second input/output surface.

In some embodiments, a first layer of refractive index-matched optical material may be formed between the first input/output surface of the prism and the PIC, and a second layer of refractive-index matched optical material may be formed between the second input/output surface of the prism and the lid.

In some embodiments, the first layer of layer of refractive-index matched optical material comprises a layer of epoxy and the second layer of refractive-index matched optical material comprises a layer of silicone gel.

In other embodiments, the first layer of layer of refractive-index matched optical material comprises a layer of silicone gel and the second layer of refractive-index matched optical material comprises a layer of epoxy. Advantages of the use of silicone gel and/or epoxy are set out earlier in this application.

In some embodiments, the back region comprises a light barrier wall and a first photodiode mounted to the substrate layer, and the second percentage of light transmitted through the third input/output surface may be scattered from the light barrier wall onto the first photodiode.

In other embodiments the back region further comprises a second photodiode mounted to the light barrier wall and may be configured to receive the second percentage of light which is transmitted through the third input/output surface.

In some embodiments the prism may be formed of a material comprising a refractive index, $n_1$, with any value in the range of 1.5 to 1.8 to inclusive. For example, the $n_1$ may be any value in the range of 1.55 to 1.75 inclusive, for example any value in the range of 1.6 to 1.7 inclusive, such as 1.65. The value of $n_1$ may be, for example, any one of the following values: 1.50, 1.51, 1.52, 1.53, 1.54, 1.55, 1.56, 1.57, 1.58, 1.59, 1.60, 1.61, 1.62, 1.63, 1.64, 1,65, 1.66, 1.67, 1.68, 1.69, 1.70, 1.71, 1.72, 1.73, 1.74, 1.75, 1.76, 1.77, 1.78, 1.79, 1.80.

In other embodiments the prism and the lid are formed of glass.

In some embodiments the substrate layer may be either a printed circuit board, PCB, of the wearable device or may be a sub-mount layer bonded to a PCB of the wearable device.

In some embodiments the substrate layer comprises: a BOX layer and a silicon layer on top of the BOX layer.

In other embodiments the prism has a total length of 1.80 mm and a total height that may be any value in the range between 1.00 mm and 1.05 mm.

In some embodiments the first input/output surface formed between the PIC and the prism may be any value in the range between 0.32 mm and 0.37 mm in length.

The invention includes the combination of the aspects and preferred features described except where such a combination is clearly impermissible or expressly avoided.

BRIEF DESCRIPTION OF THE DRAWINGS

Embodiments of the invention will now be described by way of example with reference to the accompanying drawings in which:

FIG. 3 is a side schematic of the optical assembly according to another embodiment of the present invention; FIG. 3a is a side schematic view of a portion of that optical assembly and FIG. 3b shows the complete optical assembly of that embodiment including the portion shown in FIG. 3a;

FIG. 4 is a side schematic view of the optical assembly according to another embodiment of the present invention; FIG. 4a is a side schematic of a portion of that optical assembly and FIG. 4b shows the complete optical assembly of that embodiment including the portion shown in FIG. 4a;

DETAILED DESCRIPTION

The detailed description set forth below in connection with the appended drawings is intended as a description of exemplary embodiments of an optical assembly provided in accordance with the present invention and is not intended to represent the only forms in which the present invention may be constructed or utilized.

Aspects and embodiments of the present invention will now be discussed with reference to the accompanying figures. Further aspects and embodiments will be apparent to those skilled in the art. All documents mentioned in this text are incorporated herein by reference.

Figure 1:
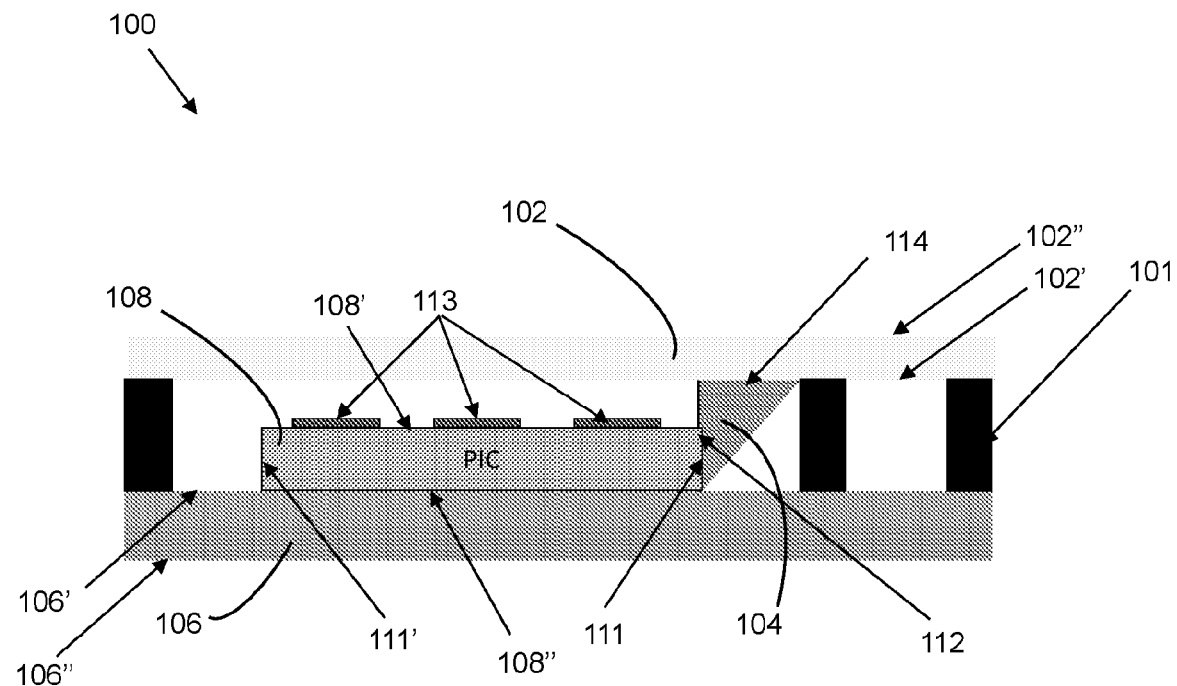
FIG. 1 is a side schematic view of the optical assembly according to an embodiment of the present invention.

FIG. 1 is a schematic view of an optical assembly 100 for use in a wearable device (not shown). The assembly 100 includes a lid 102, a prism 104, a substrate layer 106, and a photonic integrated chip (PIC) 108.

The optical assembly 100 has a layered semiconductor structure, with the bottommost layer being the substrate layer 106, an intermediate layer comprising the PIC 108, and a topmost layer comprising the lid 102. The prism 104 is coupled to second side 111 of the PIC 108, and may be considered to form part of the intermediate layer.

The substrate layer 106 has a top surface 106' facing the lid 102 and a bottom surface 106" located outside of from the assembly 100 structure. The PIC 108 has a top surface 108' that also faces the lid 102 and a bottom surface 108" that is mounted directly onto the top surface 106' of the substrate layer 106.

The lid 102 has an inner surface 102' that faces the top surface 106' of the substrate layer 106 and is located within the assembly 100 structure, and an outer surface 102" that is located outside of the assembly 100 structure and faces away from (and is located opposite to) the inner surface 102'. In the example shown, the surfaces 106' and 106" of the substrate layer 106, the surface 108' and 108" of the PIC and the surfaces 102' and 102" of the lid are all parallel or substantially parallel to each other, but it will be appreciated that in alternative embodiments (not shown), this need not be the case. In the embodiment shown in FIG. 1 (and shown the later figures), one or more optical devices 113 are mounted to the top surface 108' of the PIC 108. Three optical devices 113 are visible in the figures, however as the skilled person will appreciate, that the total number of optical devices 113 used in the optical assembly 100 may be more or less than this amount. In some embodiments, these optical devices 113 may be made from any III-V material, such as being an active III-V chip for example. In other embodiments, these optical devices 113 may be optical amplifiers, in which case, they may be Reflective Semiconductor Optical Amplifiers (RSOAs). In some embodiments, the RSOAs 113 may be wire-bonded to the top surface 108' of the PIC 108.

The PIC 108 also has two opposing sides, perpendicular (or substantially perpendicular) to the top surface 108' and bottom surface 108", which are laterally spaced apart from each other; namely a first side 111' and a second side 111. The first side 111' and the second side 111 are the left side and the right side of the PIC 108 as shown in FIG. 1, respectively. Each side 111', 111 of the PIC 108 laterally extends away from the top surface 106' of the substrate layer 106 towards the inner surface 102' of the lid 102.

The prism 104 has i) a first input/output surface 112 that is optically coupled to the PIC 108 at its second side 111, and ii) a second input/output surface 114 that is optically coupled to the lid 102 at its inner surface 102'. The second input/output surface 114 is located adjacent to the first input/output surface 112. The first input/output surface 112 is also orientated perpendicularly to the second input/output surface 114. In other embodiments (not shown) the angle between the first input/output surface 112 and the second input/output surface 114 may instead be a near perpendicular angle.

In the embodiment shown in FIG. 1, the prism 104 is mounted onto one of the laterally extended sides (i.e. the second side 111) of the PIC 108 and is also connected to the inner surface 102' of the lid 102, such that the prism 104 forms an intermediary connection between the PIC 108 and the lid 102. In other words, the prism 104 is bonded directly onto the second side 111 of the PIC 108 at the first input/output surface 112 and is also directly bonded onto the inner surface 102' of the lid 102 at the second input/output surface 114.

A plurality of struts 101 form part of a structural support of the assembly 100 and are mounted onto both the top surface 106' of the substrate layer 106 and the inner surface 102' of the lid 102. Three struts 101 are visible in the schematic shown in FIG. 1 although, as the skilled person will appreciate, that the total number of struts 101 used may be more or less than the amount shown. In alternatively embodiments, there may be no struts 101 used at all, the prism 104 instead acting as the structural support, or part of the structural support of the assembly 100.

In use, the prism 104 provides an optical path for light generated by an output (not shown in FIG. 1) of the assembly 100. In this way, during an operation of the assembly 100, the prism 104 receives an output light signal (not shown in FIG. 1) from the PIC 108 through its second side 111, and subsequently reflects a percentage of the incident light from the first input/output surface 112 to the second input/output surface 114, via total internal reflection. This is possible because the refractive index of the material forming the prism is greater than the refractive index of the surrounding air.

In some embodiments of the assembly 100 the substrate layer 106 is a printed circuit board (PCB) and the bottom surface 108" of the PIC 108 is wire-bonded onto the top surface 106' of the PCB 106.

Figure 2:
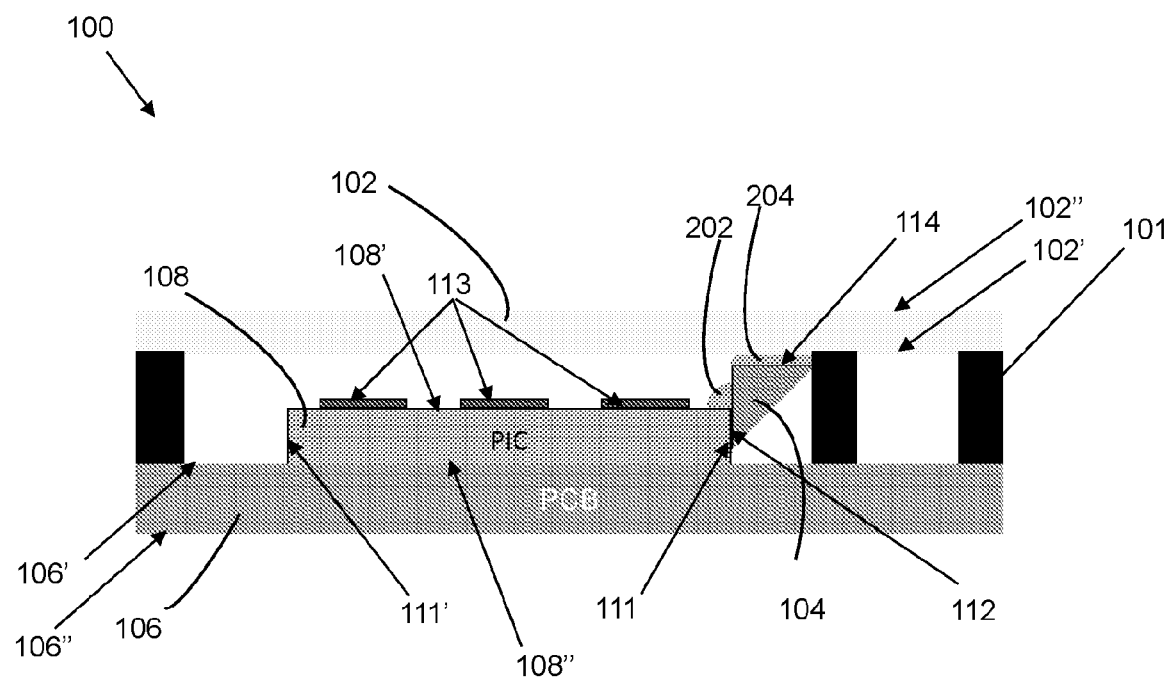
FIG. 2 is a side schematic view of the optical assembly according to another embodiment of the present invention with an addition of using different layers of refractive index-matched optical material.

FIG. 2 is a side schematic view of another embodiment of the optical assembly 100. The embodiment shown in FIG. 2 is the same as that shown in FIG. 1, with the addition of a first layer of refractive index-matched optical material 202 that is formed between the first input/output surface 112 of the prism 104 and the top surface 108' of PIC 108, and a second layer of refractive-index matched optical material 204 that is formed between the second input/output surface 114 of the prism 104 and the lid 102.

In the embodiment shown in FIG. 2, the first layer of refractive index-matched optical material 202 is deposited in an area between the first input/output surface 112 of the prism 104 and the top surface 108' of the PIC 108. In this way, the first layer of refractive index-matched optical material 202 acts as an adhesive and bonds the prism 104 to the PIC 108.

In some embodiments (not visible in FIG. 2) the first layer of refractive index-matched optical material 202 may additionally be deposited between the second side 111 of the PIC 108 and the first input/output surface 112 of the prism 104. In some alternative embodiments (not shown in the figures) the first layer of refractive index-matched optical material 202 is instead only deposited between the second side 111 of the PIC 108 and the first input/output surface 112 of the prism 104. In these embodiments, the first layer of refractive index-matched optical material 202 acts as an adhesive that bonds the prism 104 to the PIC 108.

Similarly, as also shown in FIG. 2, the second layer of refractive index-matched optical material 204 is deposited in an area between the second input/output surface 114 of the prism 104 and the inner surface 102' of the lid 102. In this way, the second layer of refractive index-matched optical material 204 also acts a separate adhesive that bonds the prism 104 to the lid 102.

In the embodiment shown in FIG. 2 the second layer of refractive index-matched optical material 204 fully extends along the entire length of the second input/output surface 114 of the prism 104 in order to form a bonding surface with the inner surface 102' of the lid 102.

In other embodiments (not shown in the figures) the second layer of refractive index-matched optical material 204 does not necessarily need to extend along the entire second input/output surface 114 and may instead only partially extend along it, depending on the adhesive strength requirements of the bond that is formed (e.g. a greater volume of deposited adhesive optical material 204 provides a stronger bond with the lid 102). In some embodiments, the first layer of layer of refractive-index matched optical material 202 is a layer of epoxy and the second layer of refractive-index matched optical material 204 is a layer of silicone gel. Alternatively, in other embodiments, use of the silicone gel and the epoxy is reversed, such that the first layer of layer of refractive-index matched optical material 202 is instead a layer of silicone gel and the second layer of refractive-index matched optical material 204 is instead a layer of epoxy. In other embodiments, other types of optical epoxies and optical gels may be used. In the embodiments, polymeric materials with index matching properties may be used.

In some embodiments, both the first layer of layer of refractive-index matched optical material 202 and the second layer of refractive-index matched optical material 204 are epoxies, for example both layers are layers of epoxy. The first layer of layer of refractive-index matched optical material 202 may be formed of a first epoxy and the second layer of refractive-index matched optical material 204 may be formed of a second epoxy. In some embodiments, the first epoxy is exactly the same as the second epoxy. In other embodiments, the first epoxy is of a different type to that of the second epoxy. In other embodiments of the optical assembly 100, the second layer of refractive index matched optical material 204 may be air. For example, the second layer of refractive-index matched optical material 204 is an air gap (or a wedge of air) that is formed between the inner surface 102' of the lid 102 and the second input/output surface 114 of the prism 104. In this embodiment, the second input/output surface 114 of the prism 104 may be coated with an anti-reflective coating.

Figure 3A:
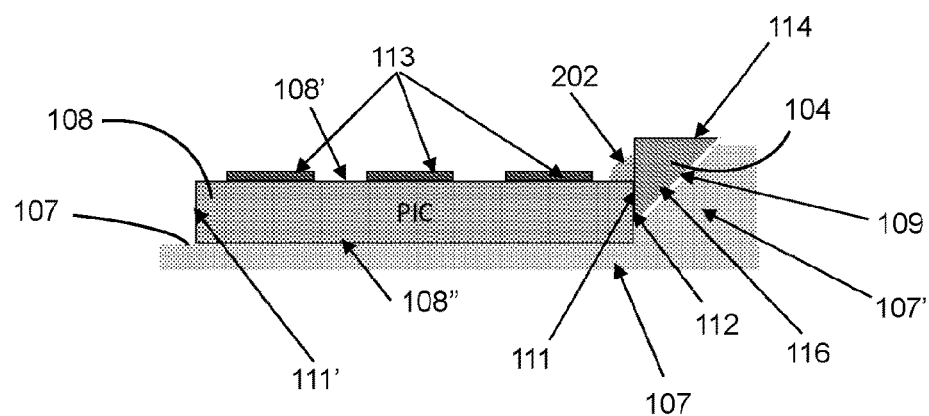
Figure 3B:
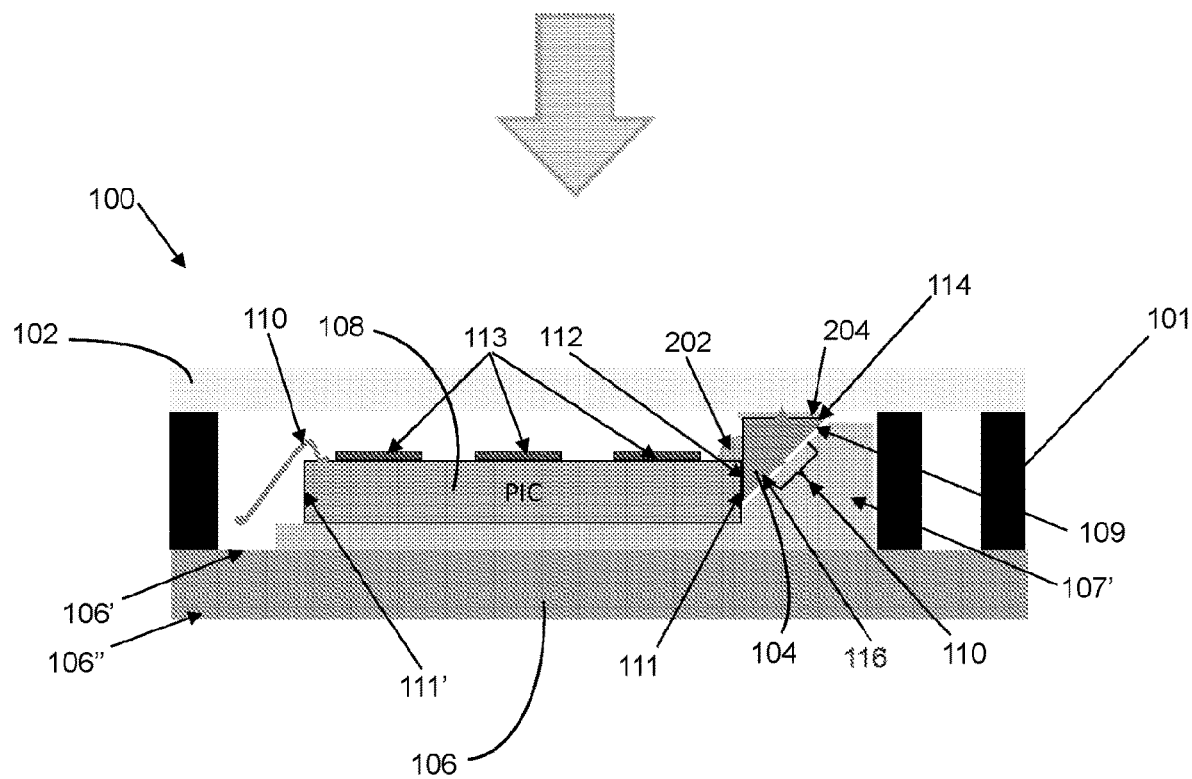

FIG. 3a is side a schematic of a portion of an optical assembly 100 according to another embodiment, whereas FIG. 3b shows the complete optical assembly 100 of that embodiment (which includes the portion shown in FIG. 3a). The embodiments shown in FIG. 3a and FIG. 3b are similar to the previously discussed embodiments, however a difference is that instead of the PIC 108 being mounted directly onto the substrate layer 106 (as shown in FIG. 1 and FIG. 2), in FIG. 3a and FIG. 3b the PIC 108 is instead mounted onto an intermediate layer 107.

The intermediate layer 107 is itself mounted (e.g. via wire-bonding) onto the bottom surface 108" of the PIC 108. The intermediate layer 107 extends along at least the entire length of the PIC 108 and forms a prism mount 107', which is an integral extension of the intermediate layer 107. The prism mount 107' may interchangeably be referred to as subcarrier 107'.

In this embodiment, the prism 104 has a total of three input/output surfaces. There is the first input/output surface 112 and the second input/output surface 114 (as previously discussed for FIG. 1 and FIG. 2), which are located adjacent to each other and orientated perpendicularly to each other. In addition, there is a third input/output surface 116 which is located opposite to both the first input/output surface 112 and the second input/output surface 114.

As previously discussed and shown in FIG. 3a and FIG. 3b, the first layer of refractive index-matched optical material 202 is deposited in an area located between the first input/output surface 112 of the prism 104 and the top surface 108' of the PIC 108. In this way, the first layer of refractive index-matched optical material 202 acts as an adhesive and bonds the prism 104 to the PIC 108. In the embodiment shown in FIG. 3b, the first layer of refractive index-matched optical material 202 is epoxy and the second layer of refractive-index matched optical material 204 is silicone gel. In other embodiments (not shown in FIG. 3b), this is reversed such the first layer of refractive index-matched optical material 202 is silicone gel and the second layer of refractive-index matched optical material 204 is epoxy.

The prism mount 107' acts as a structural support by at least (e.g. partially or fully) supporting the weight of the prism 104. In some embodiments, the prism 104 is additionally bonded to the prism support 107' along a bond surface 109 formed with a third input/output surface of the prism 116. In other embodiments (such as the embodiments shown in FIGS. 1 and 2), the prism 104 may instead be small enough (and therefore light enough) such that a subcarrier 107' is not be needed as the adhesive quality of the bond 202 is strong enough to hold prism's weight.

Referring to FIG. 3b, the optical assembly 100 of this embodiment is illustrated in operation whereby an output signal of light 110 is shown entering the PIC 108 near to its first side 111', then passing through the PIC 108 (which is not visible in the figures), and then exiting the PIC 108 at its second side 111. After which the light 100 is further shown entering the prism 104, via the first input/output surface 112, (as indicated by the horizontal arrow), and is then reflected at third input/output surface 116 (as indicated by the vertical arrow) within the prism 104 up towards the second input/output surface 114 of the prism 104.

According to one aspect of the invention, the method steps for fabricating the optical assembly 100 shown in FIG. 3b are as follows:
  Step 1) form a substrate layer 106. The substrate layer may itself be a PCB in some embodiments.
  Step 2) form the intermediate layer 107 (which includes the subcarrier 107')
  Step 3) bond the intermediate layer 107 (including the subcarrier 107') to the substrate layer 106. In some embodiments this is done by wire-bonding.
  Step 4) bond the PIC 108 to the intermediate layer 107 (including the subcarrier 107'). In some embodiments this is done by wire-bonding.
  Step 5) bond the prism 104 to the PIC 108 using a layer of epoxy 202 at the first input/output surface 112, and
  Step 6) bond the lid 102 to the prism 104 using a layer of silicone gel 204 at the second input/output surface 114.
In other embodiments, the above-mentioned method steps (1) to (6) used to fabricate the optical assembly 100 shown in FIG. 3b are reversed.
In some embodiments another method of fabricating the optical assembly comprises 100 shown in FIG. 3b are as follows:
  Step 1) form a substrate layer 106. The substrate layer may itself be a PCB in some embodiments.
  Step 2) form the intermediate layer 107 (which includes the subcarrier 107'),
  Step 3) bond the prism 104 to the PIC 108 using a layer of epoxy 202 at the first input/output surface 112,
  Step 4) bond the lid 102 to the prism 104 using a layer of silicone gel 204 at the second input/output surface 114,
  Step 5) bond the PIC 108 to the intermediate layer 107 (including the subcarrier 107'). In some embodiments this is done by wire-bonding.
  Step 6) bond the intermediate layer 107 (including the subcarrier 107') to the substrate layer 106. In some embodiments this is done by wire-bonding.

Figure 4A:
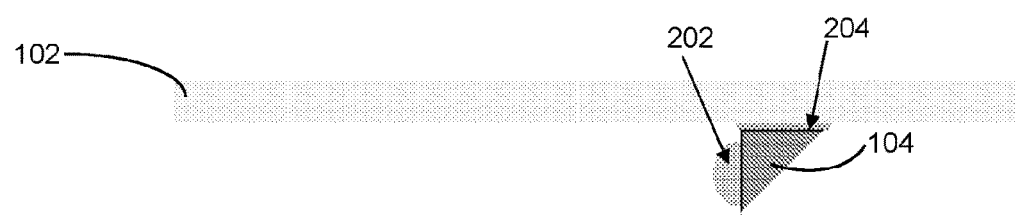
Figure 4B:
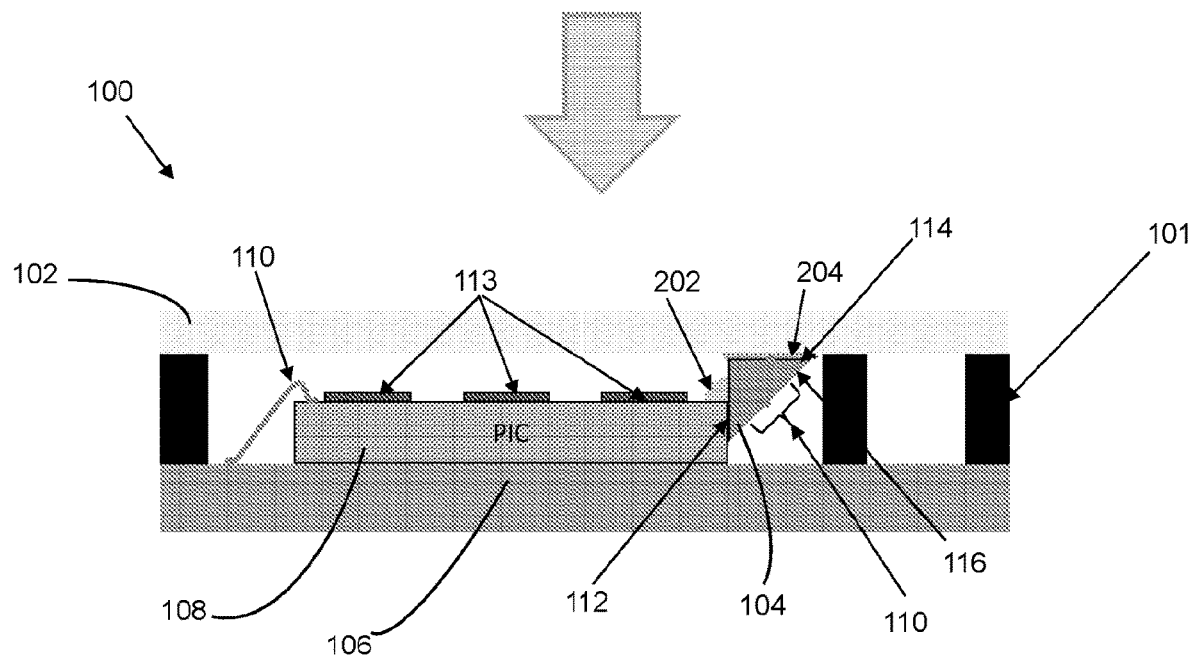

FIG. 4a is a side schematic view of a portion of an optical assembly 100 according to another embodiment, whereas FIG. 4b shows the complete optical assembly 100 of that embodiment (which includes the portion shown in FIG. 4a). The embodiments shown in FIG. 4a and FIG. 4b are similar to the embodiments shown in FIG. 3a and in FIG. 3b, respectively. However, the difference is that the PIC 108 is mounted directly onto the substrate layer 106 (as is the case in the embodiments shown in FIG. 1 and FIG. 2) and there is no intermediate layer 107 and no prism mount 107' present.

In the embodiment shown in FIG. 4b, the first layer of refractive index-matched optical material 202 is silicone gel and the second layer of refractive-index matched optical material 202 is epoxy. In other embodiments (not shown in FIG. 4b), this is reversed such the first layer of refractive index-matched optical material 202 is epoxy and the second layer of refractive-index matched optical material 204 is silicone gel.

Similarly to FIG. 3b, FIG. 4b illustrates the optical assembly 100 of this embodiment in operation whereby an output signal of light 110 is shown entering the PIC 108 near to its first side 111', then passing through the PIC 108 (which is not visible in the figures), and then exiting the PIC 108 at its second side 111. After which the light 100 is further shown entering the prism 104, via the first input/output surface 112, (as indicated by the horizontal arrow), and is then reflected at third input/output surface 116 (as indicated by the vertical arrow) within the prism 104 up towards the second input/output surface 114 of the prism 104.

According to another aspect of the invention, the method steps for fabricating the optical assembly 100 shown in FIG. 4b are as follows:
  Step 1) form the substrate layer 106. The substrate layer may itself be a PCB 106 in some embodiments.
  Step 2) bond the PIC 108 to the substrate/PCB 106. In some embodiments this is done by wire-bonding the PIC 108 to the PIC 106.
  Step 3) bond the prism 104 to the PIC 108 using a layer of silicone gel at the first input/output surface 112, and
  Step 4) bond the lid 102 to the prism 104 using a layer of epoxy at the second input/output surface 114.
In other embodiments, the above-mentioned method steps (1) to (4) used to fabricate the optical assembly 100 shown in FIG. 4b are reversed.
In some embodiments another method of fabricating the optical assembly 100 shown in FIG. 4b are as follows:
  Step 1) form the substrate layer 106. The substrate layer may itself be a PCB 106 in some embodiments.
  Step 2) bond the prism 104 to the PIC 108 using a layer of silicone gel at the first input/output surface 112,
  Step 3) bond the lid 102 to the prism 104 using a layer of epoxy at the second input/output surface 114, and
  Step 4) bond the PIC 108 to the substrate/PCB 106. In some embodiments this is done by wire-bonding the PIC 108 to the PIC 106.

Figure 5:
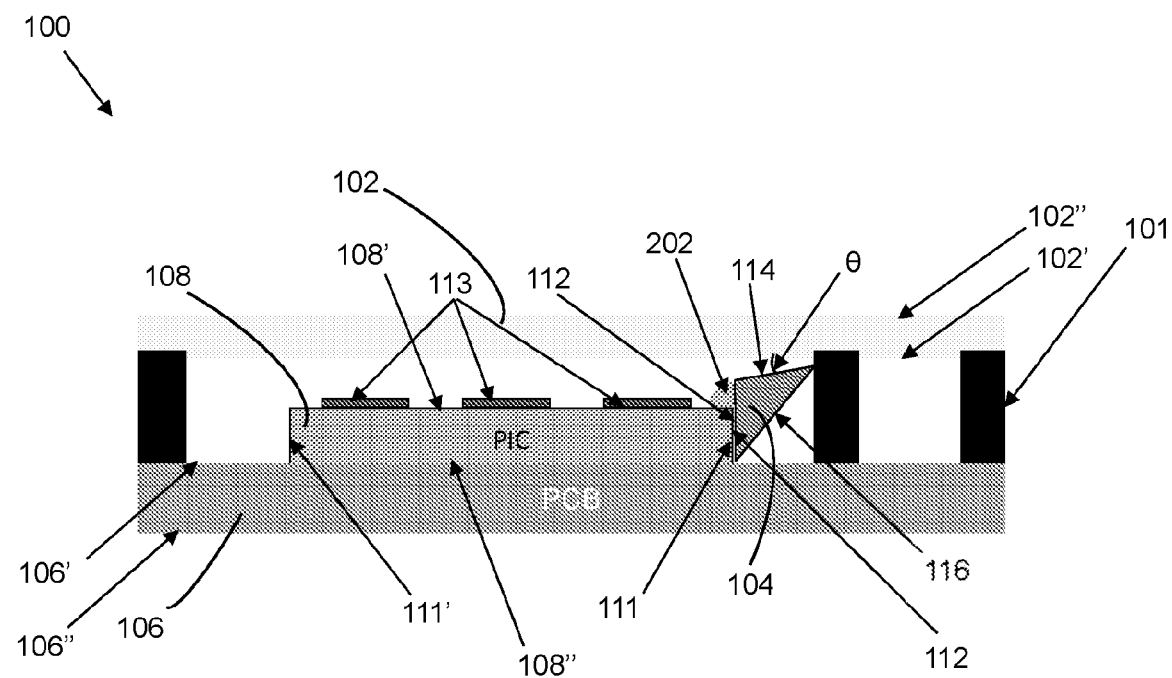
FIG. 5 a side schematic of the optical assembly according to another embodiment of the present invention, where the second input/output surface of the prism is orientated at angle θ to the lid.

FIG. 5 a side schematic of a complete optical assembly 100 according to another embodiment, which is very similar to the embodiments shown in FIG. 2, FIG. 3b, and FIG. 4b.

In the embodiment shown in FIG. 5 the second input/output surface 114 of the prism 104 is orientated at angle θ to the lid 102. The prism 104 has a total of three input/output surfaces: a first input/output surface 112, a second input/output surface 114 which is located adjacent to the first input/output surface 112, and a third input/output surface 116 which is located opposite to the first input/output surface 112. In the embodiment shown, the angle θ is 8°. Advantageously, by orientating the prism at angle θ, the optical assembly 100 can minimize interfering back reflection and eliminate the need for a polymer fill, for example. Orientating the prism at angle θ in this way also eliminates the need for use of an index matching epoxy between the prism 104 and the lid 102 as an air wedge is formed therebetween, i.e. within the cavity subtended by angle θ (i.e. is formed within the angle θ between the second input/output surface 114 of the prism 104 and the lid 102). This advantageously removes the effect of the back reflection of the light.

Figure 6:
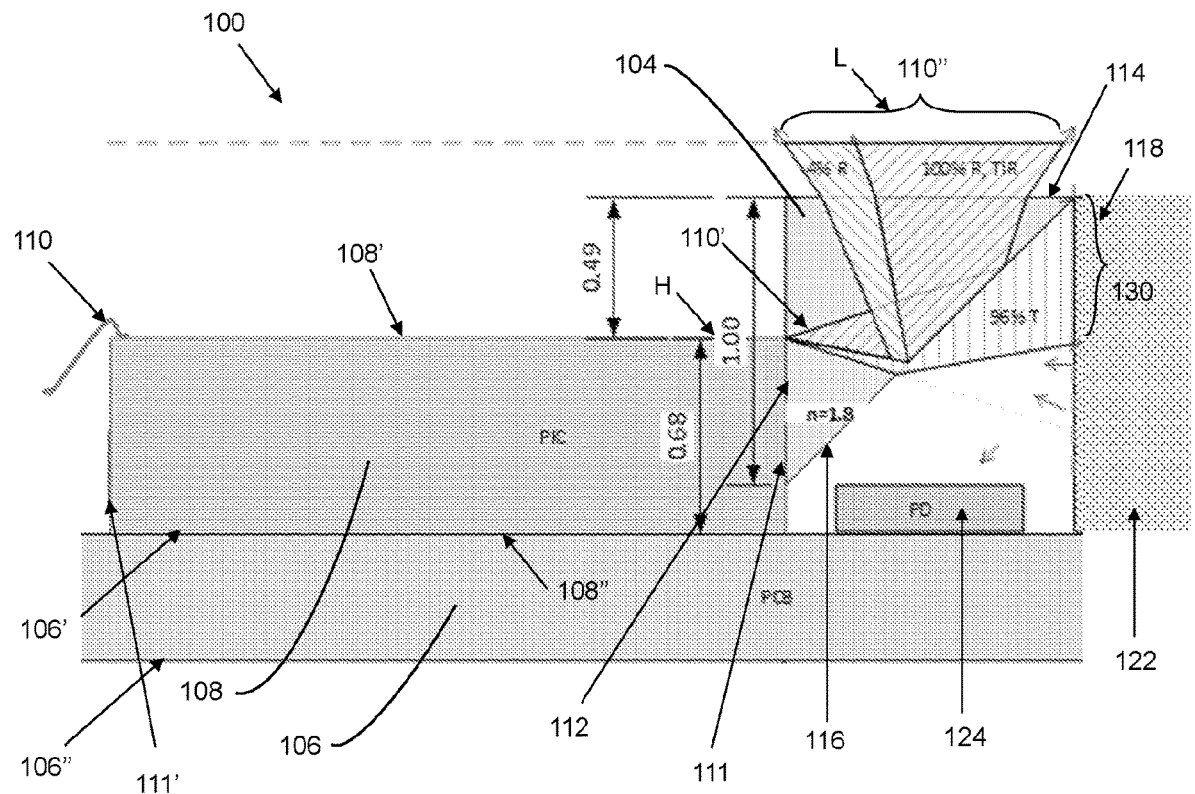
FIG. 6 shows a different embodiment of the optical assembly and illustrates a magnified area of the optical tap of the optical assembly, similar to the embodiments shown in FIG. 4b.

FIG. 6 shows a different embodiment of the optical assembly 100 and illustrates a magnified area of the optical tap of the optical assembly 100, similar to the embodiments shown in FIG. 4b.

Referring to FIG. 6, the output signal of light 110 is shown passing through the PIC 108 and the prism 104 in detail during an operation of the optical assembly 100. As shown, a light signal 110 initially enters the first side 111' of the PIC 108, then passes through the PIC 108 (not visible in the figures), and then exits the PIC 108 at its second side 111 as a light cone. After which, the light cone 110 enters the prism 104, via the first input/output surface 112, which is indicated by light cone 110' (i.e. the light cone shaded with diagonal lines).

Once the light cone passes 110' through the prism 104 it is incident on the third input/output surface 116. The third input/output surface 116 then reflects a first percentage of incident light as indicated by light cone 110" within the prism 104 up towards the second input/output surface 114.

Figure 7A:
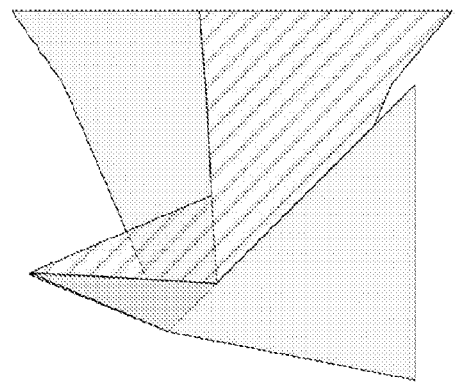
FIGS. 7A to 7C illustrate different mechanisms of reflection and transmission within the prism.
Figure 7B:
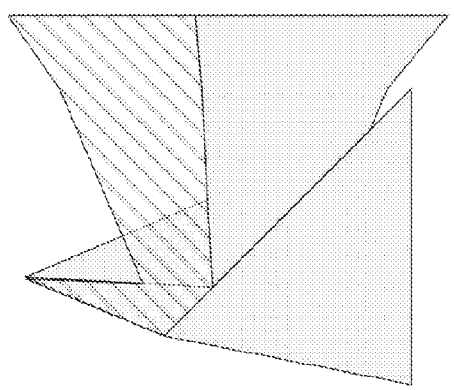
Figure 7C:
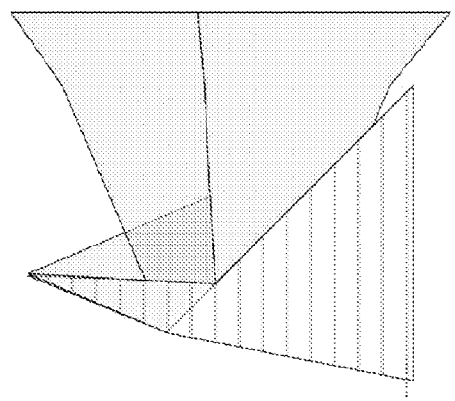

In addition, a second percentage of light, as indicated by the light cone 130 shaded with horizontal lines is transmitted through the third input/output surface into a back region 118 of the prism 104. In the embodiment shown in FIG. 7, the reflected light cone 110" comprises rays which have been totally internally reflected by the surface 116 (i.e. reflections of the rays with an angle of incidence greater than the critical angle, indicated by the diagonally shaded region in FIG. 7A), and rays which result from specular reflection at the surface 116 (i.e. reflections of those rays with an angle of incidence less than the critical angle, but only a small proportion, 4%, which underwent specular reflection, indicated by the diagonally shaded region of FIG. 7B). Light cone 110" represents the first percentage of the light. Light cone 130 comprises the rays with an angle of incidence greater less than the critical angle, which were transmitted through the third input/output surface 116. This represents the significant majority (in this case 96%) of the light incident at less than the critical angle, illustrated by the vertically shaded region of FIG. 7C.

In the embodiment shown in FIG. 6, the back region 118 further includes a light barrier wall 122 and a first photodiode 124 (labelled "PD" in FIG. 6) that is mounted to the top surface 106' of the PCB 106 (or substrate layer 106). In this embodiment, the second percentage of transmitted light 130 is shown to be scattered from the light barrier wall 122 wall onto the first photodiode 124 to be detected by that photodiode. The light barrier wall 122 may be any internal wall or region within the semiconductor structure that light cannot pass through. The light barrier wall 122 may be configured to scatter and/or reflect some (or all) of the incident transmitted light cone 130 that passes through the third input/output surface 116. The first photodiode 124 shown in FIG. 6 is an MPD that is receiving a small portion of the light entering the prism 104 in order to provide an input for an amount of signal amplification needed. The light is not scattered from the light barrier wall 122 but rather a small amount of light is reflected by the prism 104. The purpose of the light barrier wall 122 is to stop stray light from reaching the sensor photodiodes 124. In some embodiments, the light barrier wall 122 may be designed to reflect light onto the first photodiode 124. In one embodiment the light barrier wall 122 is a strut 101, as shown in assemblies illustrated in FIGS. 1 to 4.

In the embodiment shown in FIG. 6, the prism 104 is formed of a material comprising a refractive index, n, that has value of 1.8. However, in other embodiments (not shown in the figures) the refractive index, n, may be any value in the range between 1.5 and 1.8. The height of the PIC 108 from its bottom surface 108" to its top surface 108' is 0.68 mm.

The prism 104 shown in FIG. 6 has a total of three input/output surfaces. In the embodiment shown, these are all equal in length when measured from the top surface 106' of the substrate 106. The length of the first input/output surface 112, and the length of the second input/output surface 114, is 1.0 mm, and the length of the third input/output surface 116 is 1.41 mm. The height of the PIC 108 when measured from the top surface 106' of the substrate 106 is 0.68 mm. The combined height of the PIC 108 and the prism 104 when they are bonded together and when measured from the top surface 106' of the substrate 106 is 1.17 mm (i.e. 0.68 mm+0.49 mm=1.17 mm). It should be understood that the dimensions shown in FIG. 6 are to illustrate one working example and that other dimensions could also be used.

The first input/output surface 112 that is formed between the PIC 108 and the prism 104 when measured from the top surface 106' of the substrate 106 is: 0.32 mm (i.e. 1.00 mm−0.68 mm=0.32 mm). In other embodiments not shown in the figures, the first input/output surface 112 that is formed between the PIC 108 and the prism 104 when measured from the top surface 106' of the substrate 106 may be any value in the range between 0.32 mm and 0.37 mm in length.

In the embodiment shown in FIG. 6, both the lid 102 is and the prism 104 are formed of glass. In some other embodiments (not shown in the figures), the lid 102 may alternatively be made from any from any optically transparent material, such as an optically clear polymer or crystal. In other embodiments, the prism 104 may be formed of any other optically transparent materials that is also configured to refract white light into its constituent colours. In addition to glass, other possible prism materials include acrylic and fluorite, for example.

In other embodiments, the lid 102 is intentionally diffused, such as being formed of a diffuse material (e.g. formed of diffuse glass). For the example, either the inner surface 102' of the lid 102 is diffused, or the outer surface of the lid 102" is diffused, or both the inner surface 102' of the lid 102 and the outer surface of the lid 102" are diffused. Intentionally diffusing the lid 102 may be done in order to mitigate against the lid 102 becoming an etalon (also known as a Fabry-Perot interferometer or FPI). In other words, mitigating against the lid surfaces 102', 102" of the lid 102 forming parallel reflecting surfaces (or mirrors) with an optical cavity in-between.

Figure 8:
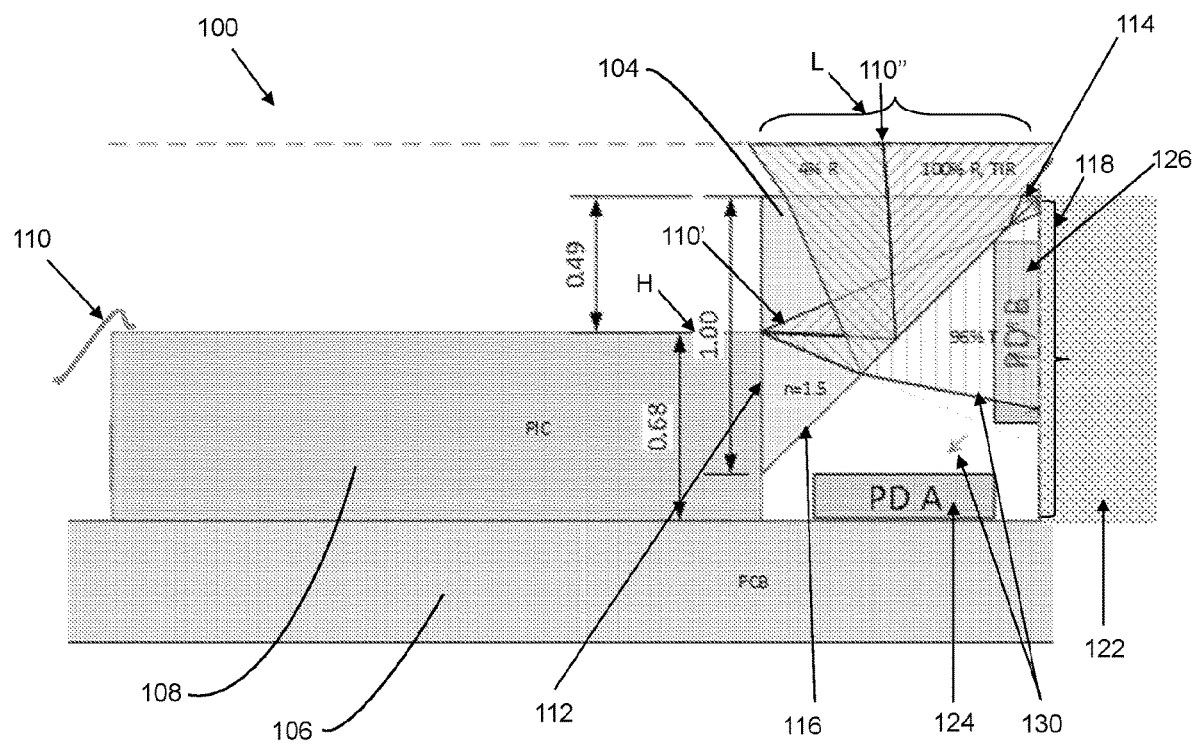
FIG. 8 shows a different embodiment of the optical assembly and illustrates a magnified area of the optical tap of the optical assembly, similar to the embodiment shown in FIG. 6.

FIG. 8 shows a different embodiment of the optical assembly 100 and illustrates a magnified area of the optical tap of the optical assembly 100, similar to the embodiment shown in FIG. 6.

In this embodiment, the back region 118 as a second photodiode 126 (labelled "PD B") mounted to the light barrier wall 122 in addition to a first photodiode 124 (labelled "PD A") which is mounted to the top surface 106' of the PCB 106 (or substrate layer 106). The second photodiode 126 is configured to receive some (or all) of the incident transmitted light cone 130 that passes through the third input/output surface 116. The light barrier wall 122 is configured to scatter and/or reflect some (or all) incident light on it. Specifically, the light barrier wall 122 is designed to reflect light onto the first photodiode 124. In one embodiment the light barrier wall 122 is a strut 101, as shown in assemblies illustrated in FIGS. 1 to 4.

In the embodiment shown in FIG. 8, the prism 104 is formed of a material comprising a refractive index, n, that has value of 1.5. The dimensions of the assembly shown in FIG. 8 are identical to that shown in FIG. 6. As is also identical to that shown FIG. 6, in the embodiment shown in FIG. 8, the reflected light cone 110" comprises rays which have been totally internally reflected by the surface 116 (i.e. reflections of the rays with an angle of incidence greater than the critical angle, indicated by the diagonally shaded region in FIG. 7A), and rays which result from specular reflection at the surface 116 (i.e. reflections of those rays with an angle of incidence less than the critical angle, but only a small proportion, 4%, which underwent specular reflection, indicated by the diagonally shaded region of FIG. 7B). Light cone 110" represents the first percentage of the light. Light cone 130 comprises the rays with an angle of incidence greater less than the critical angle, which were transmitted through the third input/output surface 116. This represents the significant majority (in this case 96%) of the light incident at less than the critical angle, illustrated by the vertically shaded region of FIG. 7C. In FIG. 8, however, the critical angle will be greater than in FIG. 6, due to the lower refractive index.

Figure 9:
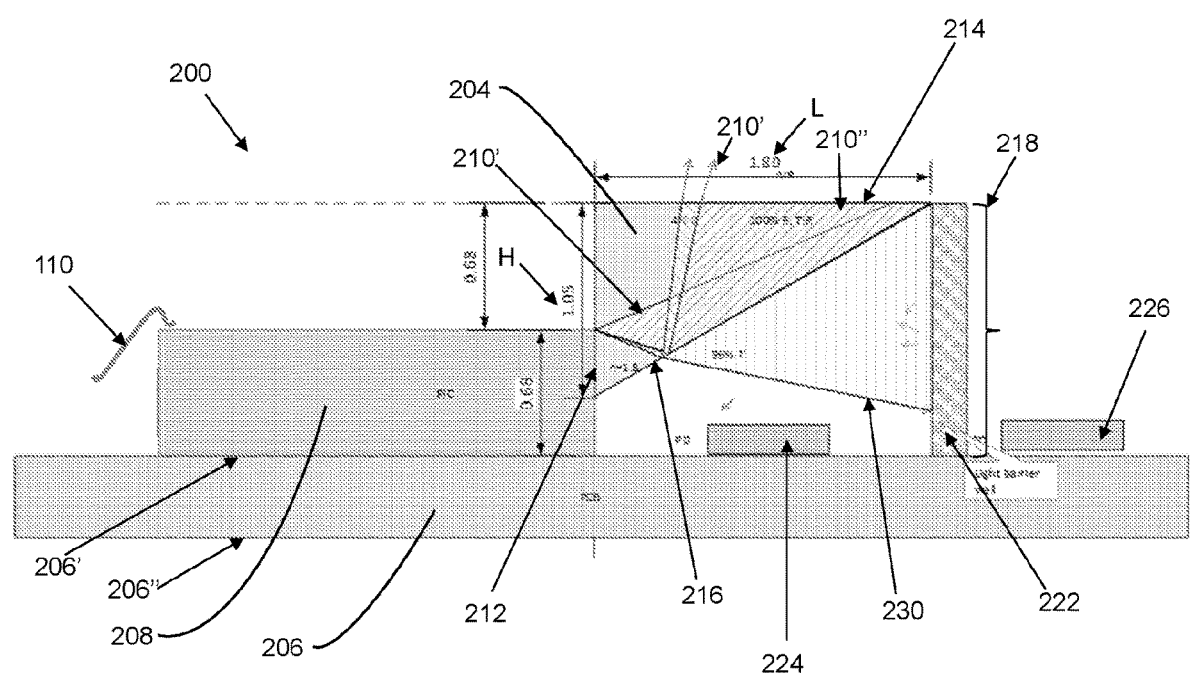
FIG. 9 shows a different embodiment of the optical assembly and illustrates a magnified area of the optical tap of the optical assembly. The embodiment shown in FIG. 9 is similar to the embodiment shown in FIG. 8, but the dimensions are different.

FIG. 9 shows a different embodiment of the optical assembly 200 and illustrates a magnified area of the optical tap of the optical assembly 200. The embodiment shown in FIG. 9 is similar to the embodiment shown in FIG. 8, however the dimensions of the assembly 200 are slightly different, as explained below. It should be understood that the dimensions shown in FIG. 8 are to illustrate one working example and that other dimensions could also be used.

The prism 204 shown in FIG. 9 has a total of three input/output surfaces which are not all equal in length. The length of the first input/output surface 212 is 1.05 mm whereas the length of the second input/output surface 214 is 1.80 mm. In this way, the length of the third input/output surface 216 is ~2.08 mm (as approximated using a Pythagorean theorem calculation).

The height of the PIC 208 when measured from the top surface 206' of the substrate 206 is 0.68 mm. The combined height of the PIC 208 and the prism 204 when they are bonded together and when measured from the top surface 206' of the substrate 206 is 1.36 mm (i.e. 0.68 mm+0.68 mm=1.36 mm).

A total height (H) of the prism 104 may be defined as the vertical distance measured from the top surface 106' of the substrate 106 between a first corner of the prism 104 (i.e. located between the first input/output surface 112 and the third input/output surface 116) and a second corner of the prism 104 (i.e. located between the first input/output surface 112 and the second input/output surface 114) when it is installed in the assembly 100.

A total length (L) of the prism 104 may be defined as the horizontal distance measured from the second side 111 of the PIC 108 between the second corner of the prism 104 (i.e. located between the first input/output surface 112 and the second input/output surface 114) and a third corner of the prism 104 (i.e. located between the second input/output surface 114 and the third input/output surface 116) when it is installed in the assembly 100.

The first input/output surface 212 that is formed between the PIC 208 and the prism 204 when measured from the top surface 206' of the substrate 206 is: 0.37 mm in length (i.e. 1.05 mm−0.68 mm=0.37 mm). In other embodiments not shown in the figures, the first input/output surface 212 that is formed between the PIC 208 and the prism 204 when measured from the top surface 206' of the substrate 206 may be any value in the range between 0.32 mm and 0.37 mm in length.

In the embodiment shown in FIG. 9, the back region 218 includes a first photodiode 224 mounted to the top surface 106' of the PCB 106 (or substrate layer 106). The light barrier wall 122 is configured to scatter and/or reflect some (or all) incident light on it. Specifically, the light barrier wall 222 is designed to reflect light onto the first photodiode 224. In one embodiment the light barrier wall 122 is a strut 101, as shown in assemblies illustrated in FIGS. 1 to 4. A second photodiode 226 is shown to be located outside of the back region 218, however in other embodiments (not shown in FIG. 9) the second photodiode 226 may be located on the light barrier wall 222 in the same as shown in the embodiment illustrated in FIG. 8.

The placement of photodiode 226 on the top surface 206' of the substrate 206, as shown in FIG. 9 may be a standard placement of that sensor photodiode (i.e. the photodiode 226 located on the opposite side of the light barrier wall 222 from the prism 204). The second photodiode 226 can be a sensor photodiode located on the other side of the light barrier wall 222 and is used to receive light reflected by another surface (e.g. the wearer's skin). In other embodiments (not shown in any of the figures) there may be more than one sensor photodiode 226 located on the opposite side of the light barrier wall 222 from the prism 204, for example located on the top surface 206' of the substrate 206.

In the embodiment shown in FIG. 8, the prism 204 is formed of a material comprising a refractive index, n, that has value of 1.5. As is identical to that shown FIG. 6 and FIG. 7 the second percentage of light is indicated by the light cone 230 (also shaded with horizontal lines) that is transmitted through the third input/output surface into a back region 218 of the prism 204. The reflected light cone 110" comprises rays which have been totally internally reflected by the surface 116 (i.e. reflections of the rays with an angle of incidence greater than the critical angle, indicated by the diagonally shaded region in FIG. 7A), and rays which result from specular reflection at the surface 116 (i.e. reflections of those rays with an angle of incidence less than the critical angle, but only a small proportion, 4%, which underwent specular reflection, indicated by the diagonally shaded region of FIG. 7B). Light cone 110" represents the first percentage of the light. Light cone 230 comprises the rays with an angle of incidence greater less than the critical angle, which were transmitted through the third input/output surface 116. This represents the significant majority (in this case 96%) of the light incident at less than the critical angle, illustrated by the vertically shaded region of FIG. 7C. In FIG. 9, the critical angle will be the same as in FIG. 8, but due to the flatter angle of the third input/output surface relative to the direction of light emerging from the PIC 108, more of the rays making up the light cone 110" have an angle of incidence greater than the critical angle, and there is therefore a greater amount of total internal reflection than in FIG. 8.

Figure 10:
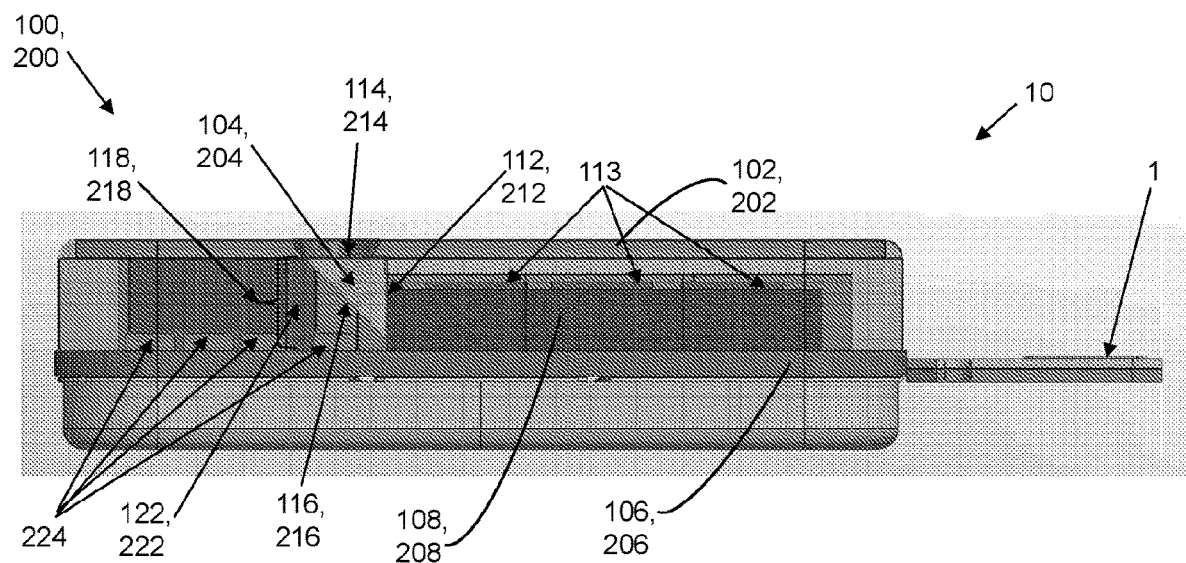
FIG. 10 is a side schematic view showing some of the circuit components of the optical assembly that electrically connect to circuitry within the wearable device, it is not inclusive of all the components of the optical assembly (such as photo diodes)

FIG. 10 is a side schematic view of a circuit component 10 (e.g. a modular circuit component 10) that electrically connects to circuitry within the wearable device (not shown in the figures) using a connecting plug 1. FIG. 10 indicates all the different locations of the various components of the optical assemblies 100, 200 as have been previously described and shown in FIGS. 1 to 8 within this circuit component 10.

Specifically, referring to FIG. 10, the various parts of the circuit component 10 are identified as follows: a lid 102, 202, a prism 104, 204; a PCB 106, 206, and a PIC 108, 208.

The prism 104, 204 has a first input/output surface 112, 212 optically coupled to the PIC 108, 208, a second input/output surface 114, 214 optically coupled to the lid 102, 202, and a third input/output surface 116, 216 optically coupled to a back region 118,218. The back region 118, 218 also includes a light barrier wall 122, 222 and a number of photodiodes 124, 224.

Although only four photodiodes 122, 222 are shown in FIG. 10, as the skilled person will appreciate, the total number of photodiodes 122, 222 used may be more or less than the amount shown.

Furthermore, only one photodiode 124, 126, 224, 226 is shown to be located in the back region 118, 218, whereas in other embodiments (not shown in the figures), there may be other photodiodes 124, 126, 224, 226 that are located or mounted onto the light barrier wall 122, 222, in a similar way to the embodiment shown in FIG. 8 has.

In some embodiments of the optical assemblies 100, 200 previously described and shown in FIGS. 1 to 9, the substrate layer 106, 206 is either a PCB of the wearable device itself, or is a PCB of the circuit component 10 (as is shown in FIG. 10), or is a sub-mount layer 107' bonded to a PCB 106 of the circuit component 10.

In other embodiments, the substrate layer 106 comprises: a BOX layer and a silicon layer mounted onto the BOX layer.

Figure 11:
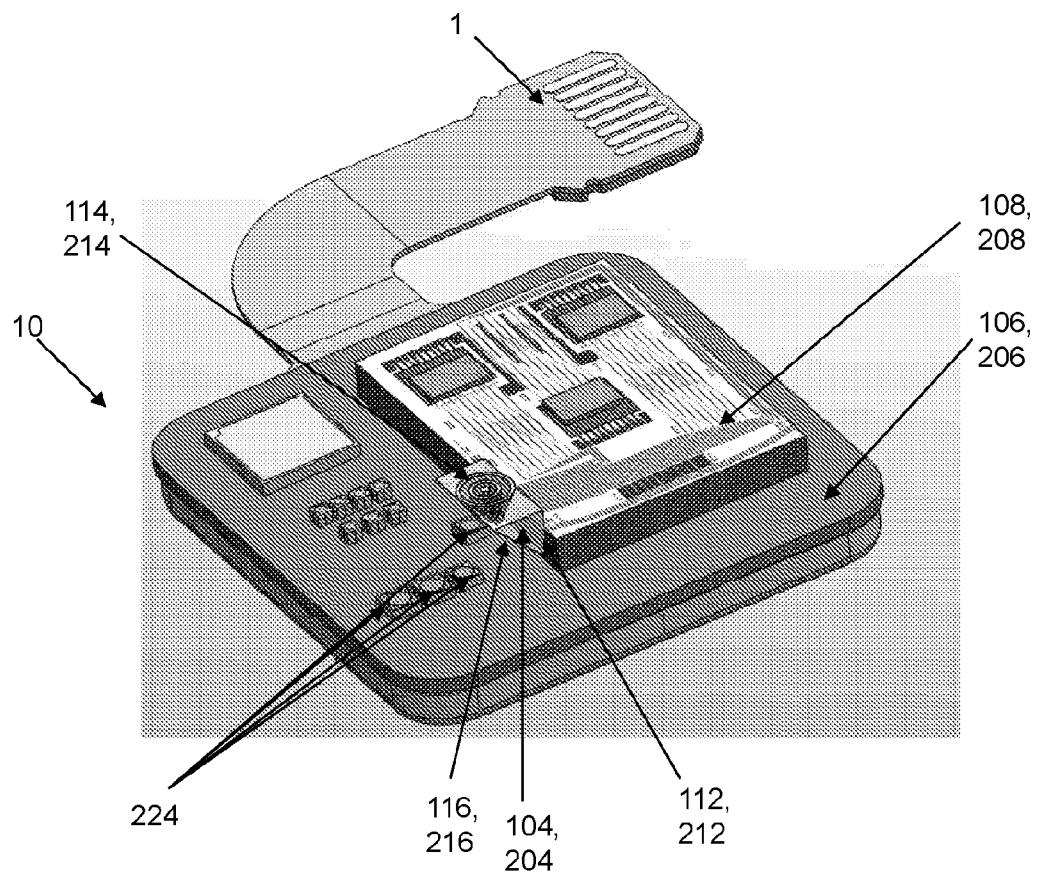
FIG. 11 is an isometric schematic view of the circuit component shown in FIG. 10.

FIG. 11 is an isometric schematic view of the circuit component 10 shown in FIG. 10 and identifies the previously described components of the optical assemblies 100, 200 from a different viewpoint and orientation.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention. It should be understood that the dimensions shown in the figures are to illustrate one or more working examples and that other dimensions could also be used.

All references referred to above are hereby incorporated by reference.

The invention claimed is:

1. An optical assembly for use in a wearable device, the assembly comprising:
   a prism, a photonic integrated chip (PIC), a substrate layer, and a lid;
   wherein the PIC is mounted onto the substrate layer;
   the prism comprising:
      i) a first input/output surface optically coupled to the PIC, and
      ii) a second input/output surface optically coupled to the lid, the second input/output surface orientated perpendicularly to the first input/output surface, and
   wherein the prism provides an optical path and reflects a first percentage of light from the first input/output surface to the second input/output surface; and
   wherein:
      a first layer of refractive index-matched optical material is formed between the first input/output surface of the prism and the PIC, and
      a second layer of refractive-index matched optical material is formed between the second input/output surface of the prism and the lid.

2. The optical assembly of claim 1; wherein the first layer of layer of refractive-index matched optical material comprises a layer of epoxy and the second layer of refractive-index matched optical material comprises a layer of silicone gel.

3. The optical assembly of claim 1; wherein the first layer of layer of refractive-index matched optical material comprises a layer of silicone gel and the second layer of refractive-index matched optical material comprises a layer of epoxy.

4. The optical assembly claim 1; wherein the substrate layer is either:
   a printed circuit board, PCB, of the wearable device, or
   a sub-mount layer bonded to a PCB of the wearable device.

5. The optical assembly claim 1; wherein the prism has a total length of 1.80 mm and a total height that is any value in the range between 1.00 mm and 1.05 mm.

6. The optical assembly claim 1; wherein the first input/output surface formed between the PIC and the prism is any value in the range between 0.32 mm and 0.37 mm in length.

7. The optical assembly of claim 1; wherein the prism further comprises (iii) a third input/output surface optically coupled to a back region, wherein:
   the prism reflects the first percentage of light at the third input/output surface towards the second input/output surface; and
   a second percentage of light is transmitted through the third input/output surface into the back region.

8. The optical assembly of claim 7; wherein the first layer of layer of refractive-index matched optical material comprises a layer of epoxy and the second layer of refractive-index matched optical material comprises a layer of silicone gel.

9. The optical assembly of claim 7; wherein the first layer of layer of refractive-index matched optical material comprises a layer of silicone gel and the second layer of refractive-index matched optical material comprises a layer of epoxy.

10. The optical assembly of claim 7; wherein the back region comprises a light barrier wall and a first photodiode mounted to the substrate layer, and wherein the second percentage of light transmitted through the third input/output surface is scattered from the light barrier wall onto the first photodiode.

11. The optical assembly of claim 10; wherein the back region further comprises a second photodiode mounted to the light barrier wall and is configured to receive the second percentage of light transmitted through the third input/output surface.

12. The optical assembly claim 7; wherein the prism and the lid are formed of glass.

13. The optical assembly claim 7; wherein the substrate layer is either:
   a printed circuit board, PCB, of the wearable device, or
   a sub-mount layer bonded to a PCB of the wearable device.

14. An optical assembly for use in a wearable device, the assembly comprising:
   a prism, a photonic integrated chip (PIC), a substrate layer, and a lid; wherein the PIC is mounted onto the substrate layer;
   the prism comprising:
      i) a first input/output surface optically coupled to the PIC,
      ii) a second input/output surface optically coupled to the lid, the second input/output surface orientated perpendicularly to the first input/output surface, and
      iii) a third input/output surface optically coupled to a back region and (ii) the second input/output surface, and wherein a second percentage of light is transmitted through the third input/output surface into the back region; and
   wherein the prism provides an optical path and reflects a first percentage of light from the first input/output surface to the second input/output surface.

15. The optical assembly of claim 14; wherein the back region comprises a light barrier wall and a first photodiode mounted to the substrate layer, and wherein the second percentage of transmitted light is scattered from the light barrier wall onto the first photodiode.

16. The optical assembly of claim 15; wherein the back region further comprises a second photodiode mounted to the light barrier wall and is configured to receive the second percentage of transmitted light through the third input/output surface.

17. An optical assembly for use in a wearable device, the assembly comprising:
   a prism, a photonic integrated chip (PIC), a substrate layer, and a lid; wherein the PIC is mounted onto the substrate layer;
   the prism comprising:
      i) a first input/output surface optically coupled to the PIC, and
      ii) a second input/output surface optically coupled to the lid, the second input/output surface orientated perpendicularly to the first input/output surface;
   wherein the prism provides an optical path and reflects a first percentage of light from the first input/output surface to the second input/output surface; and
   wherein the lid is formed of a light-diffusing material.

* * * * *